US00PP09302P

United States Patent [19]

VandenBerg

[11] Patent Number: Plant 9,302

[45] Date of Patent: Sep. 26, 1995

[54] CHRYSANTHEMUM PLANT NAMED 'KENT'

[75] Inventor: Cornelis P. VandenBerg, Salinas, Calif.

[73] Assignee: Yoder Brothers, Inc., Barberton, Ohio

[21] Appl. No.: 277,287

[22] Filed: Jul. 21, 1994

[51] Int. Cl.[6] ..... A01H 5/00

[52] U.S. Cl. ..... Plt./77

[58] Field of Search ..... Plt./77, 78

[56] References Cited

U.S. PATENT DOCUMENTS

P.P. 6,775 5/1989 Hesse ..... Plt./77

P.P. 7,488 4/1991 VandenBerg ..... Plt./77

*Primary Examiner*—Howard J. Locker

*Attorney, Agent, or Firm*—Foley & Lardner

[57] ABSTRACT

A Chrysanthemum plant named Kent particularly characterized by its flat capitulum form; decorative capitulum type; white ray floret color with cream center; diameter across face of capitulum of 79 to 83 mm when fully opened, when grown as a single stem spray cut mum; flowering response in Salinas under normal temperature is 55 to 58 days after start of short days; flowering response in Honselersdijk, The Netherlands, is 53 to 56 days from May through September; plant height is 86 cm when grown in Salinas with 13 to 18 long days prior to start of short days; height is 91 to 102 cm when grown in The Netherlands with 17 to 20 days prior to start of short days and growth regulator applications; peduncle length of the first and fourth lateral at flowering after removing the apical bud without growth regulator applications is 8 to 10 cm and 13 to 18 cm, respectively, when grown in Salinas, and 5 cm and 5 to 8 cm, respectively, when grown in The Netherlands; production of 10 to 12 laterals, each producing one terminal flower; and good stem strength in year round flowerings.

3 Drawing Sheets

The present invention comprises a new and distinct cultivar of Chrysanthemum, botanically known as *Dendranthema grandiflora,* and referred to by the cultivar name Kent.

Kent, identified as 0357 (90-928005), was originated from a cross made by Cornelis P. VandenBerg in a controlled breeding program in Salinas, Calif., in 1989.

The female parent of Kent was an unnamed seedling identified as 0361 (85-878003), and described as a flat decorative spray cut mum with an off-white ray floret color and a diameter of capitulum of 57 to 64 mm. The fenale parent was discarded from all programs on Oct. 20, 1989.

The male parent of Kent was an unnamed seedling, identified as 0790 (85-268004), and described as a flat decorative spray cut mum with many disc florets, a white ray floret color and a diameter of captiulum of 83 to 95 mm. The male parent was discarded from all programs on Dec. 7, 1990.

Kent was discovered and selected as one flowering plant within the progeny of the stated cross by Cornelis P. VandenBerg in February 1991, in a controlled environment in Salinas, Calif.

The first act of asexual reproduction of KENT was accomplished when vegetative cuttings were taken from the initial selection in May 1991 in a controlled environment in Salinas, Calif., by technicians working under supervision of Cornelis P. VandenBerg.

Horticulture examination of controlled flowerings of successive plantings has shown that the unique combination of characteristics as herein disclosed for Kent are firmly fixed and are retained through successive generations of asexual reproduction.

Kent has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Honselersdijk, The Netherlands, under greenhouse conditions which approximate those generally used in commercial greenhouse practice.

The following traits have been repeatedly observed and are determined to be basic characteristics of Kent, which in combination, distinguish this Chrysanthemum as a new and distinct cultivar:

1. Flat capitulum form
2. Decorative capitulum type.
3. White ray floret color with cream center of the flower.
4. Diameter across face of capitulum of 79 to 83 mm when fully opened, when grown as a single stem spray cut mum.
5. Flowering response in Salinas under normal temperatures is 55 to 58 days after start of short days. Flowering response in Honselersdijk, The Netherlands, is 53 to 56 days from May through September.
6. Plant height is 86 cm when grown in Salinas with 13 to 18 long days prior to start of short days; height is 91 to 102 cm when grown in The Netherlands with 17 to 20 long days prior to start of short days and growth regulator applications as required, as is common practice in The Netherlands.
7. Peduncle length of the first and fourth laterals at flowering after removing the apical bud without growth regulator applications is 8 to 10 cm and 13 to 18 cm, respectively, when grown in Salinas. Peduncle length of the first and fourth laterals when grown in The Netherlands with growth regulator applications as required is 5 cm, and 5 to 8 cm, respectively.
8. Production of 10 to 12 laterals, each producing one terminal flower.
9. Good stem strength in year-round flowerings, which is especially important during the very low light flowerings during the winter in The Netherlands.

The accompanying photographic drawings show typical inflorescence and leaf characteristics of Kent, with the colors being as nearly true as possible with illustrations of this type.

Sheet 1 is a color photograph of Kent grown as a single stem spray cut mum.

Sheet 2 is a black and white photograph of three views of the inflorescence of Kent.

Sheet 3 is a black and white photograph showing the upper and under sides of the leaves of Kent at 3 stages of development (mature, intermediate and immature). In sheets 2 and 3 a measuring tape in centimeters has been added.

Of the commercial cultivars known to the inventor, the most similar in comparison to Kent is the unpatented but well known cultivar Polaris. Refernce is made to attached Chart A, which compares certain characteristics of Kent with the same characteristics of Polaris. Kent is not being grown in Colombia, while Polaris is not being grown in The Netherlands. For that reason comparisons are made to plant material grown only in Salinas, Calif. Similar traits are capitulum form and type, and diameter across face of capitulum. Kent has a white flower with a cream center, while the flower color of Polaris is described as creamy white. When compared with Polaris, Kent has a slower flowering response to short days of 4 to 5 days, a shorter plant height and shorter peduncles. Kent has much better foliar characteristics than Polaris, with superior shipping and keeping quality of the foliage compared to Polaris.

In the following description color refrences are made to The Royal Horticultural Society Colour Chart. The color values were determined on plant material grown as a single stem spray cut mum in Honselersdijk, The Netherlands, on May 13, 1993.

Classification:

*Botanical.—Dendranthema grandiflora* cv Kent.

*Commercial.*—Decorative spray cut mum.

Inflorescence

A. Capitulum:

*Form.*—Flat.

*Type.*—Decorative.

*Diameter across face.*—79 to 83 mm when fully opened.

B. Corolla of ray florets:

*Color (general tonality from a distance of three meters).*—White with cream center of the flower, closest to 8D.

*Color (upper surface).*—155D.

*Color (under surface).*—155D.

*Shape.*—Straight, oblong, ray floret tips slightly indented, crossection concave.

C. Corolla of disc florets:

*Color (mature).*—14B.

*Color (immature).*—144B.

D. Reproductive organs:

*Androecium.*—Present on disc florets only; very few disc florets, no pollen.

*Gynoecium.*—Present on both ray and disc florets.

Plant

A. General appearance:

*Height.*—86 cm when grown in Salinas with 13 to 18 long days prior to start of short days; height is 91 to 102 cm when grown in The Netherlands with 17 to 20 long days prior to start of short days and growth regulator applications as required, as is common practice in The Netherlands.

B. Foliage:

*Color (upper surface).*—147A.

*Color (under surface).*—147B.

*Shape.*—Deeply lobed and serrated.

CHART A

COMPARISON OF KENT AND POLARIS

| CHARACTERISTIC | KENT | POLARIS |
|---|---|---|
| Ray floret color | White with cream center | Creamy white |
| Capitulum form and type | Flat decorative | Flat decorative |
| diameter across face of capitulum | 79 to 83 mm | 76 to 83 mm |
| Flowering response | 55 to 58 days | 51 to 53 days |
| Plant height | 86 cm | 94 to 104 cm |
| Peduncle length: | | |
| First lateral | 8 to 10 cm | 14 to 15 cm |
| Fourth lateral | 13 to 18 cm | 18 to 20 cm |

COMPARISONS MADE OF PLANTS GROWN AS SINGLE STEM SPRAY CUT MUMS IN SALINAS, CALIFORNIA

I claim:

1. A new and distince Chrysanthemum plant named Kent as described and illustrated.

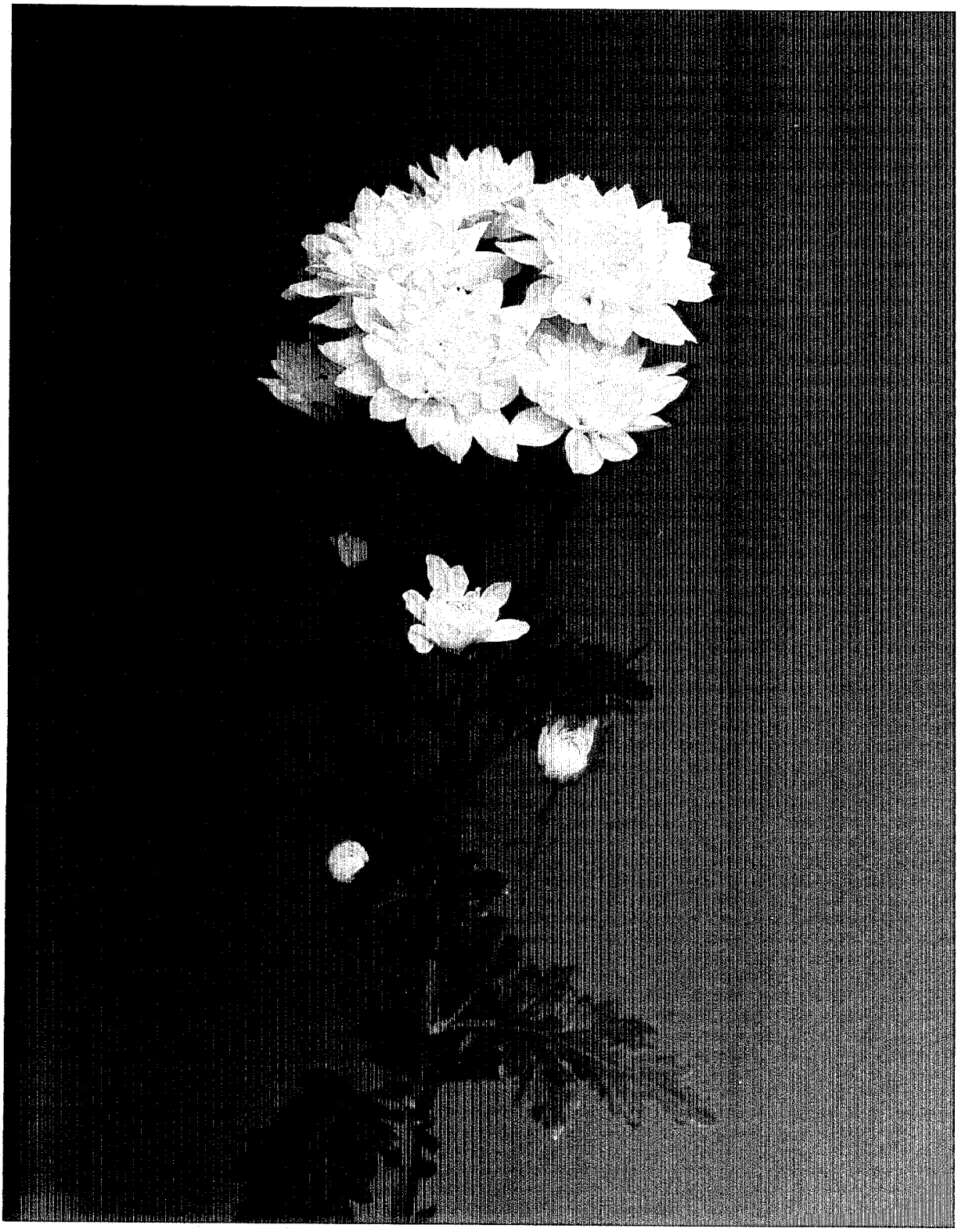

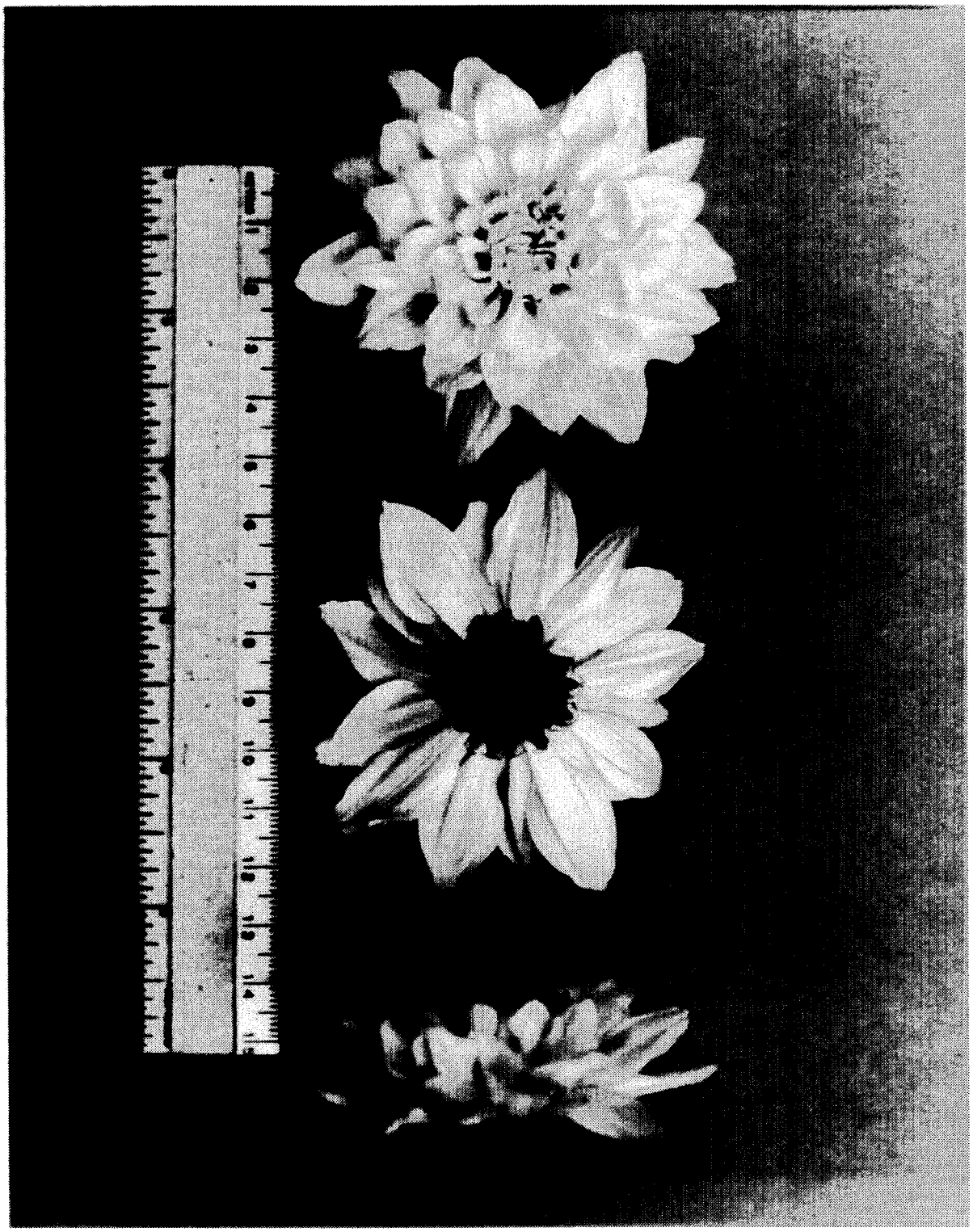

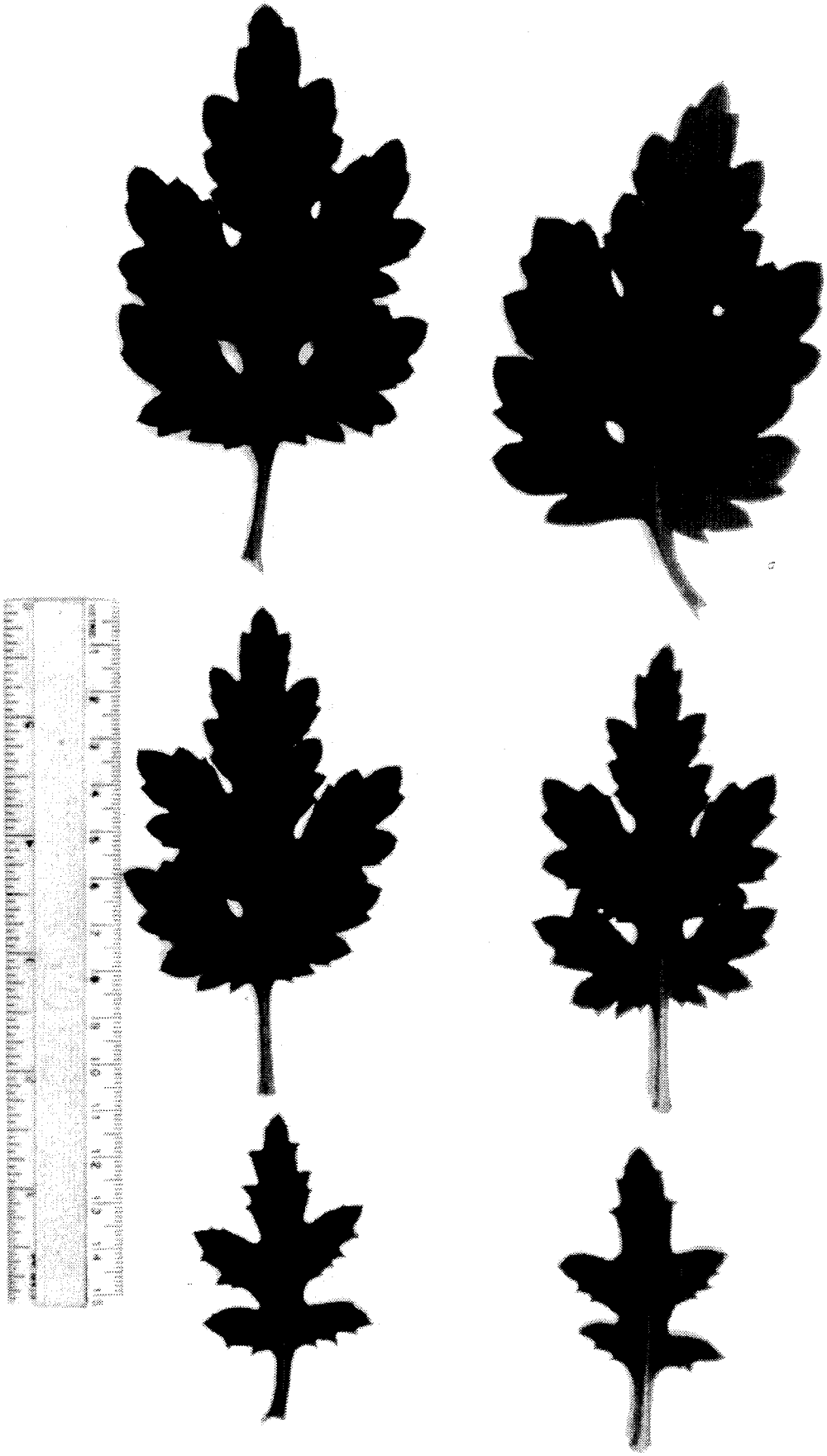

* * * * *